United States Patent [19]

Borkenstein

[11] 4,080,170

[45] Mar. 21, 1978

[54] ALCOHOL RETAINER CARTRIDGE AND METHOD FOR USING SAME

[76] Inventor: Robert F. Borkenstein, 821 S. High St., Bloomington, Ind. 47401

[21] Appl. No.: 721,619

[22] Filed: Sep. 20, 1976

[51] Int. Cl.² .......................................... G01N 33/16
[52] U.S. Cl. ............................. 23/232 R; 23/254 R
[58] Field of Search ............... 23/259, 254 R, 232 R, 23/255 R; 128/2 C

[56] References Cited

U.S. PATENT DOCUMENTS

| | | | |
|---|---|---|---|
| 2,097,650 | 11/1937 | Stampe | 23/254 R |
| 2,192,140 | 2/1940 | McCreary | 23/259 |
| 2,631,088 | 3/1953 | Guild | 23/254 R |
| 2,813,010 | 11/1957 | Hutchins | 23/254 R X |
| 3,437,449 | 4/1969 | Luckey | 23/254 R |
| 3,443,904 | 5/1969 | Hill | 23/254 R X |
| 3,522,009 | 7/1970 | Borkenstein | 23/254 R X |

Primary Examiner—Robert M. Reese
Attorney, Agent, or Firm—Woodard, Weikart, Emhardt & Naughton

[57] ABSTRACT

An alcohol retainer cartridge and method for using same are disclosed herein comprising calcium sulfate as an adsorbent for alcohol. The cartridge includes calcium sulfate contained within a tube between pieces of filter paper. At one end of the tube is a disc having a central aperture smaller than the interior of the tube, the disc resting against an inwardly extending lip of the tube. A spring clip bearing against the interior wall of the tube retains the filter paper at the other end. A sample of the alcohol in a person's breath is obtained by passing an amount of the person's breath, preferably about 52 milliliters, through the calcium sulfate, preferably in the amount of about 0.5 grams. The alcohol is adsorbed by the calcium sulfate and may be subsequently assayed.

18 Claims, 5 Drawing Figures

U.S. Patent  March 21, 1978  4,080,170
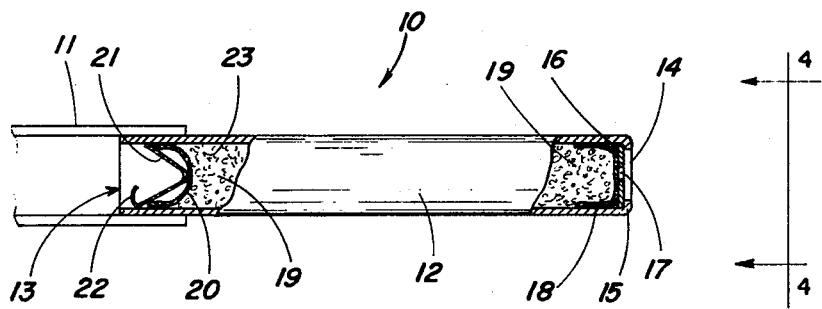
Fig. 1
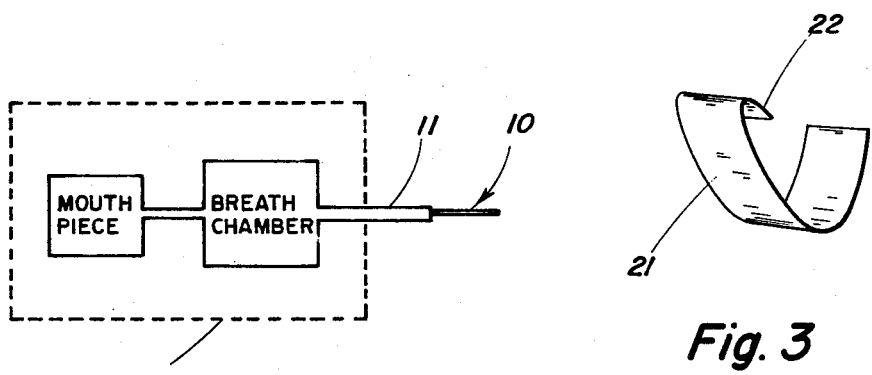
Fig. 2
Fig. 3
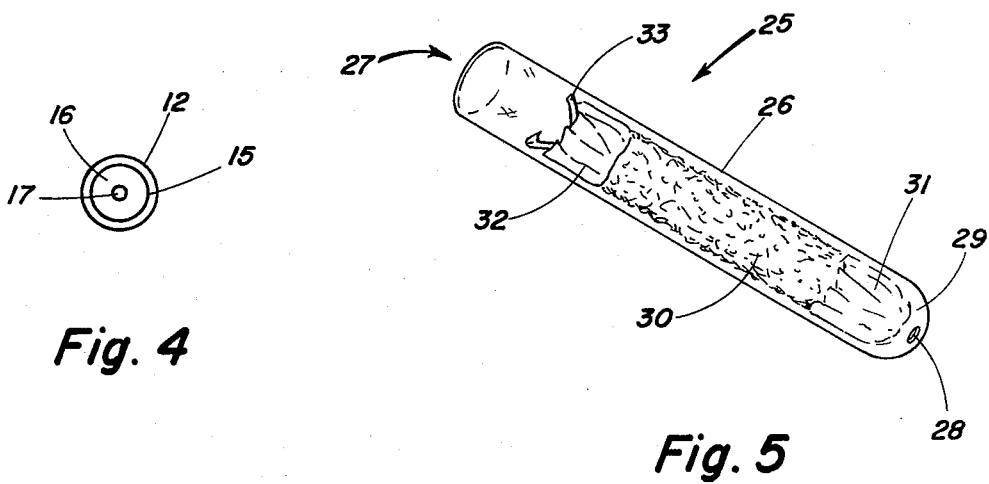
Fig. 4
Fig. 5

ALCOHOL RETAINER CARTRIDGE AND METHOD FOR USING SAME

BACKGROUND OF THE INVENTION

1. Field of the Invention

This invention relates to devices and methods for determining the amount of alcohol in a person's breath, and more particularly to the retention of the alcohol for later evaluation.

2. Description of the Prior Art

The adsorption of alcohol from a gas such as air may be important for a variety of reasons. A primary application is in the field of law enforcement, in which breath analysis devices are used to test alcohol content of a person's breath.

Breath analysis devices of various types are known in the art. In the apparatus known as the "Breathalyzer", a 52½ ml. sample of breath is collected in a heated reservoir and is then bubbled through an ampoule containing a solution of potassium dichromate in a 50% aqueous sulfuric acid solution. The alcohol content is determined by photometric measurement of the reduction of the dichromate by alcohol. Comparable devices are disclosed in U.S. Pat. No. 3,544,273, issued to McConnaughey on Dec. 1, 1970; U.S. Pat. No. 3,303,840, issued to Etzlinger on Feb. 14, 1967; and U.S. Pat. No. 3,238,783, issued to Wright on Mar. 8, 1966. The specification in the McConnaughey patent discloses a representative operation of these types of devices, and is hereby incorporated by reference. In the McConnaughey apparatus, the breath sample is passed through a tube containing a chromium compound held between glass wool plugs. The chromium compound changes color in response to alcohol in the breath sample. This and other prior art devices for analysis of breath alcohol uniformly incorporate a chemical reagent which reacts to the alcohol, rather than retaining it for later assaying.

Some compounds are known to adsorb certain other materials. Calcium sulfate has been recognized to be a desiccant substance which will adsorb water from air or other materials. This property is disclosed in U.S. Pat. Nos. 2,813,010, issued to Hutchins on Nov. 12, 1957; U.S. Pat. No. 2,758,719, issued to Line on Aug. 14, 1956; and, U.S. Pat. No. 2,593,132, issued to Gannon on Apr. 15, 1952. Calcium sulfate has also been used to remove water from alcohol in order to concentrate the alcohol, as is described in Volume 14, pages 34-37 of the Transactions of the Indiana Institute of Chemical Engineers (1961-1962) and pages 16-21 of Chemical Process Design, Symposium, Bangalore, Indiana (1963). These sources, however, do not disclose the property of calcium sulfate to adsorb alcohol itself from air or a similar material.

Other known desiccants include calcium chloride, magnesium sulfate, sodium sulphate and silica gel, as disclosed in U.S. Pat. No. 1,789,194, issued to Rockwell on Jan. 13, 1931; and the Hutchins patent and publications previously cited. These sources do not discuss the potential for any of these desiccants to adsorb alcohol. However, it has been known to use magnesium perchlorate and calcium chloride to retain breath alcohol for later assaying.

In the use of various desiccants, a number of containers have been devised to contain the desiccant. The Rockwell device utilizes a cannister in which a spring bearing against the cannister top holds a screen against a cotton pad which contacts the desiccant. A similar structure is described in U.S. Pat. No. 2,575,483, issued to Bethig on Nov. 20, 1951, and in the Gannon and Line patents previously cited. The use of a pad, glass wool, paper and/or a screen positioned adjacent a desiccant is disclosed in U.S. Pat. No. 3,008,540, issued to Gibson on Nov. 14, 1961; U.S. Pat. No. 2,682,315, issued to Evans on June 29, 1954; U.S. Pat. No. 2,225,990, issued to Henry on Dec. 24, 1940; and U.S. Pat. No. 1,585,113, issued to Robert on May 18, 1926; and also in the Hutchins and Line patents discussed previously. None of these patents however, disclose a structure which is simply constructed for retaining a small portion of material and which permits the contents to be readily discharged for further treatment.

SUMMARY OF THE INVENTION

One embodiment of the present invention is an alcohol retainer cartridge which comprises an elongated tube having a first end and a second end, calcium sulfate contained within the tube between the first and second ends, and means for retaining the calcium sulfate within the tube. A sample of breath is passed through the calcium sulfate and the alcohol in the breath is adsorbed therefrom.

It is an object of the present invention to provide a simple and inexpensive container for retaining calcium sulfate for adsorbing alcohol.

Another object of the present invention is to provide a container as described and which permits the contents to be easily removed for further treatment.

A further object of the present invention is to provide a container of the above-described type and which provides for limiting the flow of the breath sample therethrough to prevent channeling of the breath within the calcium sulfate.

A still further object of this invention is to provide a container as described and which may be utilized in conjunction with a breath analysis device to retain alcohol from the breath sample for subsequent assaying.

It is still another object of the present invention to provide a method for retaining the alcohol in a sample of breath for subsequent assaying.

Further objects and advantages of the present invention will be apparent from the figures and description which follow.

BRIEF DESCRIPTION OF THE DRAWINGS

FIG. 1 is a partial cross-sectional view of a preferred embodiment of the alcohol retainer cartridge of the present invention.

FIG. 2 is a schematic representation of a breathalyzer utilizing the alcohol retainer cartridge of the present invention.

FIG. 3 is a perspective view of the spring clip utilized by the present invention.

FIG. 4 is a front view of the alcohol retainer cartridge of the present invention taken along line 4—4 in FIG. 1 in the direction of the arrows.

FIG. 5 is a perspective view of an alternate embodiment of the alcohol retainer cartridge of the present invention.

DESCRIPTION OF THE PREFERRED EMBODIMENTS

For the purposes of promoting an understanding of the principles of the invention, reference will now be made to the embodiments illustrated in the drawings and specific language will be used to describe the same.

It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring in particular to the figures, there is shown an alcohol retainer cartridge 10 according to the present invention. In use, cartridge 10 is connected to a source of the gas containing the alcohol desired to be adsorbed. This may be conveniently accomplished as by frictional fit within a tube 11 connected to the source of the gas. In FIG. 2 there is shown a schematic representation of a breath analysis device 24 to which cartridge 10 may be connected. Device 24 comprises a mouth piece into which the subject person exhales the breath sample, the sample being retained within the breath chamber. The sample is then discharged by suitable means through tube 11 and cartridge 10.

Cartridge 10 includes a tube 12 having an inlet opening 13 and an outlet opening 14. In the preferred embodiment, a disc 16 (FIG. 1) is positioned near the outlet opening 14 and rests against an inwardly-extending annular flange 15 which forms a lip on tube 12. Disc 16 includes a central aperture 17 through which the breath sample exits from cartridge 10. A portion of filter paper 18 is positioned against disc 16 and retains the calcium sulfate particles 19 at one end of cartridge 10. Another portion of filter paper 20 is positioned at the other end of the calcium sulfate 19. Paper 20 is held in cartridge 10 by a spring clip 21 which bears against opposite portions of interior wall 23 of tube 12. Clip 21 includes a lip 22 which may be grasped to facilitate removal of clip 21 when desired.

In FIG. 5 there is shown an alternate embodiment of the alcohol retainer cartridge. Cartridge 25 comprises a container 26 having an inlet opening 27 and an outlet opening 28. Outlet opening 28 is smaller than opening 27 and is defined by tapered portion 29 of container 26. Calcium sulfate granules 30 are held within container 26 at one end by filter paper 31 retained by tapered portion 29, and at the other end by filter paper 32 held by spring clip 33.

The calcium sulfate has been found to adsorb alcohol readily from a person's breath or the like. Calcium sulfate further is suitable for use with a breath analysis device because it does not interfere with the traditional assay techniques for alcohol. Calcium chloride, for example, causes problems in gas chromatography assaying because it gets hot when added to water and would prematurely evolve adsorbed alcohol. Calcium chloride is therefore not suitable as an alcohol adsorbent since the alcohol would be evolved by the adsorption of water due to the calcium chloride being a deliquescent (water adsorbent). Magnesium sulfate, as another example, is not a suitable adsorbent for these purposes because it melts at the temperature needed to drive off the alcohol in analysis techniques.

A particular form of calcium sulfate used in accordance with the present invention is available under the trademark "Drierite." This product is anhydrous, which facilitates use of the calcium sulfate since the presence of moisture interferes with the ready removal of the material from the cartridge due to caking. Preferably, the amount of the breath sample in milliliters is about one hundred times the amount of calcium sulfate expressed in grams. A known amount of the subject's breath, preferably about 50 milliliters, is flowed through the calcium sulfate, preferably in an amount from about 0.1 grams to about 5 grams. The amount of calcium sulfate for adsorbing the alcohol in a breath sample of about 50 ml. is more preferably from about 0.25 grams to about 1 gram, and most preferably is about 0.5 grams.

The filter paper 18 and 20, or 31 and 32, serves several functions. The filter paper prevents the granular calcium sulfate from passing through the cartridge openings, and especially prevents the loss of fine calcium sulfate particles which could otherwise affect the subsequent analysis accuracy. Another important function of the paper is to control the flow of the breath sample through the cartridge. In particular, the filter paper controls the flow of the breath sample sufficiently that back pressure does not exist at the calcium sulfate, and significant channeling of the sample through the calcium sulfate does not occur. In this regard, other materials similar in use to filter paper may be employed to fulfill these functions. Any paper or other fibrous material, or other porous material such as compacted glass wool, would also be suitable. For the purposes of this disclosure and the claims, this variety of materials useful in conjunction with the present invention are referred to as finely-porous materials.

In use, a known amount, preferably about 50 ml., of a person's breath is flowed through the calcium sulfate contained in the cartridge. The calcium sulfate adsorbs the alcohol in the breath sample and retains it for subsequent assaying. When analysis is to be performed, the calcium sulfate may be easily discharged from the cartridge. A lip on the spring clip lodged near the inlet opening of the cartridge may be readily engaged by any suitable tool or implement and the clip is then removed. A small rod is then inserted through the outlet opening and forces the filter paper and calcium sulfate out through the inlet opening. In the preferred embodiment of the cartridge, disc 16 is also plunged through the cartridge to assure full and easy discharge of the calcium sulfate. The calcium sulfate may then be analyzed as desired, such as by dichromate analysis or gas chromatography.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

The invention claimed is:

1. The combination which comprises:
   a device for the analysis of the alcohol content of breath, said device including means for obtaining a sample of a person's breath; and
   means for collecting the alcohol present in the breath sample, said collecting means including an elongated tube connected to said breath analysis device and having a first end and a second end, calcium sulfate contained within said tube between the first and second ends and means for retaining said calcium sulfate within said tube.

2. The combination of claim 1 in which said retaining means includes a first portion of finely-porous material located adjacent the first end of said tube, a second portion of finely-porous material located adjacent the second end of said tube.

3. The combination of claim 1 which further includes means for limiting the flow of a gas through said calcium sulfate, said flow limiting means being positioned at one end of said calcium sulfate.

4. The combination of claim 1 in which said retaining means includes a spring clip bearing against opposite portions of the interior of said tube and located adjacent the first end of said tube.

5. The combination of claim 1 in which the amount of calcium sulfate is from about 0.25 grams to about 1 gram.

6. The combination of claim 5 in which the amount of calcium sulfate is about 0.5 grams.

7. The combination of claim 1 in which said retaining means includes a disc located within said tube adjacent the second end, said disc including a passageway substantially smaller in area than the interior of said tube, said tube including an inwardly-extending projection against which said disc rests.

8. The combination of claim 7 which further includes means for limiting the flow of a gas through said calcium sulfate, said flow limiting means being positioned at one end of said calcium sulfate, said flow limiting means including said disc and the passageway therethrough.

9. The combination of claim 8 in which said flow limiting means and said retaining means include a first portion of finely-porous material located adjacent the first end of said tube, said flow limiting means and said retaining means further comprising a second portion of finely-porous material located adjacent the second end of said tube between said calcium sulfate and said disc.

10. The combination of claim 9 in which said retaining means includes a spring clip bearing against opposite portions of the interior of said tube and located adjacent the first end of said tube.

11. In a breath analysis device for determining the amount of alcohol in a person's breath, the improvement comprising the use of calcium sulfate to adsorb the alcohol in the breath sample for later evaluation.

12. The improvement of claim 11 in which the breath analysis device includes a chamber in which the sample of a person's breath is collected, and which further comprises:

an alcohol retainer cartridge connected to said chamber, said cartridge including an elongated tube having a first end and a second end, calcium sulfate contained within said tube between the first and second ends, and means for retaining said calcium sulfate within said tube, said breath analysis device further including means for flowing the breath sample from said chamber through said cartridge.

13. A method for obtaining a sample of the amount of alcohol in a person's breath which comprises flowing a known amount of the person's breath through calcium sulfate.

14. The method of claim 13 and also comprising the step of providing an elongated tube in which calcium sulfate is contained, said flowing comprising flowing the person's breath through the elongated tube in which said calcium sulfate is contained.

15. The method of claim 13 in which the known amount of the person's breath expressed in milliliters is about one hundred times the amount of calcium sulfate expressed in grams.

16. The method of claim 13 in which the known amount of the person's breath is about 50 milliliters and the amount of calcium sulfate is from about 0.1 grams to about 5 grams.

17. The method of claim 16 in which the amount of calcium sulfate is from about 0.25 grams to about 1 gram.

18. The method of claim 17 in which the amount of calcium sulfate is about 0.5 grams.

* * * * *